(12) United States Patent
Syed (10) Patent No.: US 9,636,244 B2
(45) Date of Patent: May 2, 2017

(54) APPARATUS AND METHOD FOR PROXIMAL TO DISTAL STENT DEPLOYMENT

(71) Applicant: Mubin I. Syed, Spingfield, OH (US)

(72) Inventor: Mubin I. Syed, Spingfield, OH (US)

( * ) Notice: Subject to any disclaimer, the term of this patent is extended or adjusted under 35 U.S.C. 154(b) by 79 days.

(21) Appl. No.: 14/683,101

(22) Filed: Apr. 9, 2015

(65) Prior Publication Data

US 2016/0296355 A1    Oct. 13, 2016

(51) Int. Cl.
*A61F 2/966* (2013.01)

(52) U.S. Cl.
CPC ...... *A61F 2/966* (2013.01); *A61F 2002/9665* (2013.01); *A61F 2230/0069* (2013.01)

(58) Field of Classification Search
CPC .. A61F 2/95; A61F 2/954; A61F 2/962; A61F 2/966; A61F 2002/9517; A61F 2002/9522; A61F 2002/9528; A61F 2002/9534; A61F 2002/9665
See application file for complete search history.

(56) References Cited

U.S. PATENT DOCUMENTS

| 4,243,040 | A | * | 1/1981 | Beecher | ........... A61B 17/22032 |
| | | | | | 604/271 |
| 5,098,707 | A | | 3/1992 | Baldwin et al. | |
| 5,293,772 | A | | 3/1994 | Carr, Jr. | |
| 5,344,426 | A | * | 9/1994 | Lau | ........................ A61F 2/92 |
| | | | | | 606/198 |
| 5,571,135 | A | * | 11/1996 | Fraser | ...................... A61F 2/95 |
| | | | | | 606/198 |
| 5,651,366 | A | | 7/1997 | Liang et al. | |
| 5,662,703 | A | * | 9/1997 | Yurek | ...................... A61F 2/95 |
| | | | | | 606/194 |
| 5,669,924 | A | | 9/1997 | Shaknovich | |
| 5,690,644 | A | * | 11/1997 | Yurek | ...................... A61F 2/95 |
| | | | | | 606/198 |
| 5,718,702 | A | | 2/1998 | Edwards | |

(Continued)

FOREIGN PATENT DOCUMENTS

WO    WO96/36269    11/1996
WO    2011/106502    9/2011

(Continued)

OTHER PUBLICATIONS

International Search Report issued in International Application No. PCT/US2013/071271 dated Feb. 10, 2014, 2 pages.

(Continued)

*Primary Examiner* — Ryan J Severson
(74) *Attorney, Agent, or Firm* — Nixon Peabody LLP (57) ABSTRACT

Methods and devices for delivering a stent in a proximal to distal fashion are disclosed. The delivery device includes a sheath catheter, an outer catheter and an inner catheter over a guide wire. A crimped stent is positioned over the distal end of the outer catheter and is held in place by a lubricous elastic membrane attached to a retractable ring. The retractable ring is connected to pull wires and slidably deployed between the inner and outer catheters. The proximal end of the stent is aligned at the treatment location, and the lubricous elastic membrane is pulled back into the space between inner catheter and outer catheter, releasing and deploying the stent from its proximal to its distal end.

20 Claims, 5 Drawing Sheets

(56) References Cited

U.S. PATENT DOCUMENTS

| | | | |
|---|---|---|---|
| 5,720,735 A | 2/1998 | Dorros | |
| 5,807,330 A | 9/1998 | Teitelbaum | |
| 5,957,901 A | 9/1999 | Mottola et al. | |
| 6,027,462 A | 2/2000 | Greene et al. | |
| 6,059,813 A * | 5/2000 | Vrba | A61F 2/01 606/198 |
| 6,238,410 B1 * | 5/2001 | Vrba | A61F 2/01 606/198 |
| 6,544,278 B1 * | 4/2003 | Vrba | A61F 2/01 606/192 |
| 6,663,613 B1 | 12/2003 | Evans et al. | |
| 6,780,174 B2 | 8/2004 | Mauch | |
| 6,808,520 B1 | 10/2004 | Fouirkas et al. | |
| 6,837,881 B1 | 1/2005 | Barbut | |
| 6,929,633 B2 | 8/2005 | Evans et al. | |
| 6,942,682 B2 * | 9/2005 | Vrba | A61F 2/01 606/192 |
| 7,393,358 B2 * | 7/2008 | Malewicz | A61F 2/966 606/108 |
| 7,758,624 B2 | 7/2010 | Dorn et al. | |
| 7,763,010 B2 | 7/2010 | Evans et al. | |
| 7,766,961 B2 | 8/2010 | Patel et al. | |
| 7,842,026 B2 | 11/2010 | Cahill et al. | |
| 7,955,370 B2 * | 6/2011 | Gunderson | A61F 2/966 623/1.11 |
| 8,092,509 B2 | 1/2012 | Dorn et al. | |
| 8,202,309 B2 * | 6/2012 | Styrc | A61F 2/95 623/1.11 |
| 8,241,241 B2 | 8/2012 | Evans et al. | |
| 8,343,181 B2 | 1/2013 | Duffy et al. | |
| 8,535,290 B2 | 9/2013 | Evans et al. | |
| 8,721,714 B2 * | 5/2014 | Kelley | A61F 2/2436 623/2.11 |
| 8,740,971 B2 | 6/2014 | Iannelli | |
| 8,986,241 B2 | 3/2015 | Evans et al. | |
| 9,314,499 B2 | 4/2016 | Wang et al. | |
| 2001/0003985 A1 | 6/2001 | Lafontaine et al. | |
| 2001/0049534 A1 | 12/2001 | Lachat | |
| 2002/0077691 A1 * | 6/2002 | Nachtigall | A61F 2/90 623/1.12 |
| 2002/0123698 A1 | 9/2002 | Garibotto et al. | |
| 2002/0156518 A1 | 10/2002 | Tehrani | |
| 2003/0088187 A1 | 5/2003 | Saadat et al. | |
| 2004/0147837 A1 | 7/2004 | Macaulay et al. | |
| 2005/0043779 A1 | 2/2005 | Wilson | |
| 2005/0113862 A1 | 5/2005 | Besselink et al. | |
| 2006/0025752 A1 | 2/2006 | Broaddus et al. | |
| 2006/0025844 A1 * | 2/2006 | Majercak | A61F 2/95 623/1.11 |
| 2006/0030923 A1 * | 2/2006 | Gunderson | A61F 2/966 623/1.11 |
| 2006/0200221 A1 * | 9/2006 | Malewicz | A61F 2/966 623/1.11 |
| 2006/0257389 A1 | 11/2006 | Binford | |
| 2006/0270900 A1 | 11/2006 | Chin et al. | |
| 2007/0038061 A1 | 2/2007 | Huennekens et al. | |
| 2007/0118151 A1 | 5/2007 | Davidson et al. | |
| 2007/0129719 A1 | 6/2007 | Kendale et al. | |
| 2008/0039746 A1 | 2/2008 | Hissong et al. | |
| 2008/0194993 A1 | 8/2008 | McLaren et al. | |
| 2008/0281398 A1 * | 11/2008 | Koss | A61F 2/95 623/1.12 |
| 2009/0177035 A1 | 7/2009 | Chin | |
| 2009/0270975 A1 | 10/2009 | Gifford, III et al. | |
| 2009/0319017 A1 | 12/2009 | Berez et al. | |
| 2010/0024818 A1 | 2/2010 | Stenzler et al. | |
| 2010/0030165 A1 | 2/2010 | Takagi et al. | |
| 2010/0030256 A1 | 2/2010 | Dubrul et al. | |
| 2010/0069852 A1 * | 3/2010 | Kelley | A61F 2/2436 604/264 |
| 2010/0168583 A1 | 7/2010 | Dausch et al. | |
| 2010/0185161 A1 | 7/2010 | Pellegrino et al. | |
| 2010/0185231 A1 | 7/2010 | Lashinski | |
| 2010/0204708 A1 | 8/2010 | Sharma | |
| 2010/0268067 A1 | 10/2010 | Razzaque et al. | |
| 2010/0272740 A1 | 10/2010 | Vertegel et al. | |
| 2011/0009943 A1 * | 1/2011 | Paul | A61B 17/12109 623/1.11 |
| 2011/0034987 A1 * | 2/2011 | Kennedy | A61F 2/95 623/1.11 |
| 2011/0071394 A1 | 3/2011 | Fedinec | |
| 2011/0224773 A1 | 9/2011 | Gifford et al. | |
| 2011/0230830 A1 | 9/2011 | Gifford, III et al. | |
| 2011/0270375 A1 | 11/2011 | Hartley et al. | |
| 2012/0016343 A1 | 1/2012 | Gill | |
| 2012/0034205 A1 | 2/2012 | Alkon | |
| 2012/0035590 A1 | 2/2012 | Whiting et al. | |
| 2012/0209375 A1 | 8/2012 | Madrid et al. | |
| 2012/0220942 A1 | 8/2012 | Hall et al. | |
| 2012/0289945 A1 | 11/2012 | Segermark | |
| 2013/0131777 A1 | 5/2013 | Hartley et al. | |
| 2013/0296773 A1 | 11/2013 | Feng et al. | |
| 2013/0331819 A1 | 12/2013 | Rosenman et al. | |
| 2013/0331921 A1 | 12/2013 | Roubin | |
| 2014/0031925 A1 | 1/2014 | Garrison et al. | |
| 2014/0142427 A1 | 5/2014 | Petroff | |
| 2015/0018942 A1 | 1/2015 | Hung et al. | |
| 2015/0174377 A1 | 6/2015 | Syed | |
| 2015/0190576 A1 | 7/2015 | Lee et al. | |
| 2015/0201900 A1 | 7/2015 | Syed | |
| 2015/0245933 A1 | 9/2015 | Syed | |
| 2015/0352331 A1 | 12/2015 | Helm, Jr. | |
| 2015/0366536 A1 | 12/2015 | Courtney et al. | |
| 2015/0374261 A1 | 12/2015 | Grunwald | |
| 2016/0008058 A1 | 1/2016 | Hu et al. | |
| 2016/0038724 A1 | 2/2016 | Madsen et al. | |
| 2016/0120509 A1 | 5/2016 | Syed | |

FOREIGN PATENT DOCUMENTS

| | | |
|---|---|---|
| WO | WO2012/030101 | 8/2012 |
| WO | 2014081947 | 5/2014 |
| WO | WO2014/197839 | 12/2014 |
| WO | 2016164215 | 10/2016 |

OTHER PUBLICATIONS

Written Opinion issued in International Application No. PCT/US2013/071271 dated Feb. 10, 2014, 5 pages.

International Preliminary Report on Patentability issued in International Application No. PCT/US2013/071271 dated May 26, 2014, 6 pages.

Office Action issued in U.S. Appl. No. 13/750,920 dated Apr. 8, 2015.

Response to Office Action in U.S. Appl. No. 13/750,920 dated Aug. 10, 2015.

Supplemental Response to Office Action in U.S. Appl. No. 13/750,920 dated Nov. 2, 2015.

Office Action in U.S. Appl. No. 13/750,920 dated Nov. 5, 2015.

Response to Office Action in U.S. Appl. No. 13/750,920 dated Feb. 11, 2016.

Beckman, Michele G. et al., "Venous thromboembolism: a public health concern"; Am J Prev Med. Apr. 2010;38(4 Suppl): S495-501.

Meunier, Jason M., et al., Individual Lytic Efficacy of Recombinant Tissue Plasminogen Activator in an in-vitro Human Clot Model: Rate of "Nonresponse" Acad Emerg Med. May 2013; 20(5): 449-455.

Tripathi, Ramesh C., et al. "Use of Tissue Plasminogen Activator for Rapoid Dissolution of Fibrin and Blood Clots in the Eye After Surgery for Claucomoa and Cataract in Humans" Drug Development Research; vol. 27, Issue 2, pp. 147-159, 1992.

Office Action in U.S. Appl. No. 13/750,920 dated Aug. 31, 2016.

International Search Report / Written Opinion issued in Int'l Application No. PCT/US2016/024795 dated Aug. 30, 2016, 14 pages.

International Search Report / Written Opinion issued in Int'l Application No. PCT/US2016/024794 dated Jul. 1, 2016, 10 pages.

International Search Report / Written Opinion issued in Int'l Application No. PCT/US2016/047163 dated Oct. 28, 2016, 9 pages.

(56) References Cited

OTHER PUBLICATIONS

International Search Report and Written Opinion issued for International Application No. PCT/US2016/047165 dated Jan. 5, 2017, 13 pages.

* cited by examiner

Figure 1

Figure 2
(Cross section A-A)

APPARATUS AND METHOD FOR PROXIMAL TO DISTAL STENT DEPLOYMENT

BACKGROUND

1. Field

The invention generally relates to methods and an apparatus for the deployment of stents, and more particularly to, methods and an apparatus for aligning and installing stents with high accuracy by proximal-to-distal deployment, enabled for accurate proximal edge placement within the lumen.

2. Related Art

Use of stents, to overcome weakness in the walls of lumens within the human body and to open up blood vessels constricted by plaque to improve blood flow, have been in existence for some time now. These stents comprise both open stents and medicated or covered stents. The accurate placement of these stents within the lumen is a very difficult, but accurate placement of these stents is important to repair any defective regions on the side wall of the lumens. In addition, stents are used to keep the blood vessels with plaque deposit open to prevent problems related to blood supply to the organs.

Many deployment devices have been developed for accurate placement of stents in human body lumens. Many of the deployment devices are used for placement of the newer self-expanding type of stents. Most placement devices have an inner catheter with a section designated to hold a crimped stent over it at the distal end, covered by an outer catheter slidably deposed over the inner catheter to hold the crimped stent in place until deployment. A guide wire through and within the inner catheter is used as a guide to insert and guide the stent deployment device to the location where the stent will be deployed. Once at the location, the outer catheter is pulled back from over the stent to expose and deploy the stent at the location. Typically, the deployment is a distal-to-proximal deployment or a central-to-edge deployment.

A major drawback of these devices is that they install the stent in the distal-to-proximal direction. There are several scenarios where the typical distal-to-proximal deployment is highly undesirable, and a means of positioning the stent to have one end at an exact proximal location, requiring a proximal-to-distal deployment, would be extremely advantageous. Placement of the proximal edge of the stent accurately at a proximal location is critical in certain scenarios, including, for example, deployment of the self-expanding stent at a location where a side branch of a lumen originates and the side branch is not to be covered; deployment of the stent so that it overlaps another previously installed stent proximally; and deployment of the stent to cover the ostia of a lumen. The proximal to distal deployment will also be very useful in iliac stenting and during Endovascular (abdominal aortic) aneurysm repair (EVAR) procedures.

Although some proximal to distal stent placement devices have been disclosed, they do not provide the ease of placement or the capability to pre-define and establish the position of the proximal edge of the stent with respect to the location of the lumen prior to deployment for an accurate proximal-to-distal placement.

SUMMARY

The following summary of the invention is included in order to provide a basic understanding of some aspects and features of the invention. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

In accordance with one aspect of the invention, a stent deployment system is disclosed that includes an inner catheter slideably movable over a guide wire; an outer catheter slideably moveable over the inner sheath such that an interspace if formed between the inner catheter and the outer catheter; an expandable stent crimped on the outer sheath; a lubricous elastic membrane removably covering the stent, the lubricous elastic membrane having a proximal end and a distal end; a ring slidably deployed over the inner catheter and retractable into the interspace, the ring attached to the distal end of the lubricous elastic membrane; a plurality of pull wires connected to the ring, for retracting the ring and elastic membrane into the interspace.

The system may further include a sheath catheter, the outer catheter slideably movable within the sheath catheter. The system may further include the guide wire.

The plurality of pull wires may include two pull wires.

The system may further include a pull mechanism connected to the proximal end of the pull wires and for applying a pullback force for retracting the ring and elastic membrane into the interspace.

The membrane may be invertible.

In accordance with a further aspect of the invention, a method of using the deployment device of claim 1 to deploy a stent in a proximal-to-distal fashion is disclosed.

In accordance with another aspect of the invention, a method is disclosed that includes delivering a stent deployment device to a treatment location, the stent deployment device comprising an inner catheter, an outer catheter, a stent attached to the outer catheter, a membrane covering the stent, a ring attached to a distal end of the membrane, and a plurality of wires attached to the ring and extending through a space between the inner catheter and the outer catheter; aligning a proximal edge of the stent to the treatment location; and retracting the ring and the membrane into the space between the inner catheter and the outer catheter using the pull wires to expand the stent from its proximal end to its distal end.

The membrane may cover and retain the stent in a crimped state over the outer catheter prior to retraction.

The ring and pull wires may pull the membrane to retract the membrane from over the stent in a proximal to distal fashion.

Refraction of the ring may invert and invaginate the membrane.

The method may further include sliding the outer catheter our from within the sheath catheter to expose the stent.

The method may further include forming a small opening in the groin region of the patient to gain access to the femoral artery; and inserting a guide wire into the femoral artery.

The method may further include advancing a tip of a guide wire to the treatment location; and anchoring the guide wire at the treatment location.

The guide wire may be advanced under guidance from X-ray imaging. The stent deployment device may be delivered to the treatment location over the guide wire. The proximal edge of the stent may be aligned to the treatment location using X-ray imaging.

A pull mechanism may be used to apply a pull force to the pull wires to retract the ring and membrane. The pull force applied to the ring may be uniform.

The method may further include removing the stent deployment device, leaving the stent accurately deployed in place within the body lumen

BRIEF DESCRIPTION OF THE DRAWINGS

The accompanying drawings, which are incorporated into and constitute a part of this specification, illustrate one or more examples of embodiments and, together with the description of example embodiments, serve to explain the principles and implementations of the embodiments.

DETAILED DESCRIPTION

An apparatus and corresponding method to achieve a reverse stent deployment installation, from proximal to distal, with the capability to monitor the proximal placement location prior to deployment, to ensure accurate placement with critical proximal stent positioning is also disclosed herein. The stent delivery and deployment device described herein is used to accurately place a stent within a lumen through a procedure using a stent deployment method that is proximal to distal allowing accurate placement of the proximal edge. The deployment device also lets the operator check and align the proximal and distal position of the stent to allow for accurate positioning within the lumen.

The stent deployment device includes an inner catheter, an outer catheter and a sheath catheter over a guide wire. The outer catheter tube is deployed in a slidable/movable manner within the sheath catheter tube. An accurately adjustable slide mechanism associated with the outer catheter and the sheath catheter enable the accurate positioning of the outer catheter with reference to the distal end of the sheath catheter. The guide wire, which is inserted into the inner catheter, provides a guide for the deployment device to the correct location.

A crimped stent is deposed over the distal end of the outer catheter. The crimped stent is held in its compressed position on the outer catheter by a lubricous elastic membrane attached to a retractable ring with pull wires. The highly lubricous elastic and transparent membrane is in the form of a cover. One end of the cover is attached to the ring deployed over the inner catheter, such that it can move freely within the space between the outer and inner catheters. The ring itself can be drawn back into the interspace between the inner and outer catheters using a multiple of pull wires that extend within the space between the inner and outer catheters. Using the ring it is possible to pull in the lubricous elastic membrane covering the stent and release the stent from its proximal to distal end. The pull wires extend in the inter space between the inner catheter and the outer catheter. A pull back mechanism is connected to the proximal ends of the pull wires and attached to the proximal end of the deployment device. The pull back mechanism is used to exert uniform pull force on the ring for retracting the ring when needed. Once proximal end placement of the stent is achieved by extending and positioning the outer catheter, the lubricous elastic membrane is pulled back by pulling the ring back using the pull wires into the space between the inner catheter and the outer catheter, releasing the stent in a controlled fashion from proximal-to-distal end. The self-expanding stent is allowed to expand.

The accurate placement of the stent is accomplished by initially fixing the location of the proximal end. The wires connected to the ring to which the lubricous elastic membrane is connected are drawn in, pulling the lubricous elastic membrane with it into the interspace of the inner and outer catheters. As the membrane gets drawn in, it releases the proximal end of the stent allowing it to deploy at the location from the proximal-to-distal end. Since the stent was aligned before the membrane is pulled back, the location of the proximal end can be accurately fixed.

Additional visual and irrigation capability are provided through the catheters as known to those of skill in the art to visually observe the placement of the stent and to irrigate the location and the stent as needed.

The proximal to distal deployable stent and deployment mechanism disclosed herein may be used in the proximal superficial femoral artery (SFA). It will be appreciated that the deployment system may be used in a number of other procedures, including, but not limited to, during iliac stenting and during Endovascular (abdominal aortic) aneurysm repair (EVAR).

This proximal to distal stent is also usable for accurate deployment of stent during venous stenting, to avoid stenting across major vein bifurcations (the confluence of the internal jugular vein with the innominate vein when stenting from an upper extremity approach). Accuracy of stent placement is necessary to prevent stenting across the internal jugular vein in dialysis patients when treating a stenosis of the innominate or subclavian veins which are central and peripheral to the internal jugular vein respectively. This becomes critical because the internal jugular vein is literally the lifeline for dialysis catheter placement if the upper extremity dialysis fistula fails in these patients.

Figure 1:
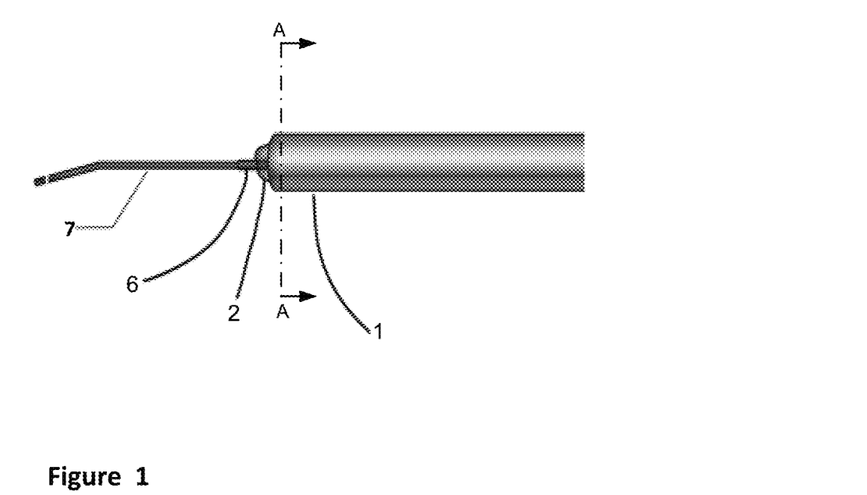
FIG. 1 is a side view of a stent deployment device for insertion into the lumen according to one embodiment of the invention.
Figure 2:
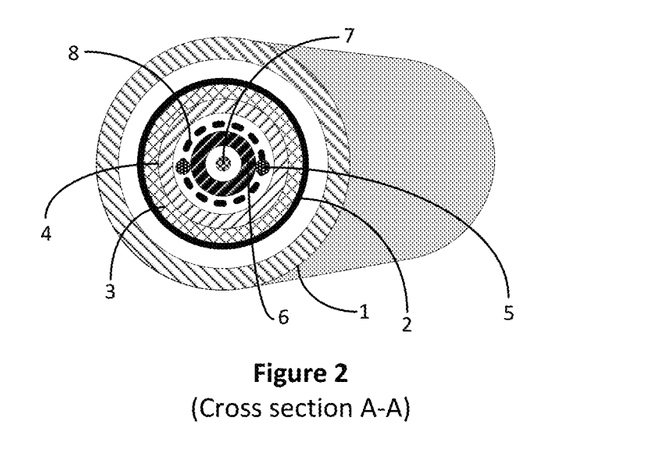
FIG. 2 is a cross section (A-A) view of the stent deployment device of FIG. 1 according to one embodiment of the invention.

FIG. 1 shows a diagram of a stent deployment device 100, and FIG. 2 is a cross-sectional view 200 of the device 100 at section A-A. As shown in FIGS. 1 and 2, the stent deployment device 100 includes a sheath catheter 1, an elastic lubricous membrane 2, a stent 3, an outer catheter 4, pull wires 5, an inner catheter 6, a guide wire 7, and a ring 8.

The guide wire 7 is used to ensure that the stent deployment device 100 is guided through the body lumen from entry point to the correct location. The guidance and stent deployment is typically conducted under X-ray monitoring.

The expandable stent 3 is shown in a crimped state in FIGS. 1 and 2, placed over the outer catheter 4. The crimped stent is covered by the elastic lubricous membrane 2 that is in the form of an open ended bag. The elastic lubricous material forming the elastic lubricous membrane 2 is typically formed of a reinforced stretchable nylon that is coated by a lubricant material. The inner catheter 6 is positioned over the guide wire 7, typically having a stainless steel wire of a 0.014 inch diameter. The sheath catheter 1 provides protection to the elastic-lubricous-membrane 2, covering the crimped-stent 3. It will be appreciated that although the sheath catheter 1 is shown in FIGS. 1 and 2, it is not essential for the deployment device 100 and the deployment device 100 may be used without the sheath catheter 1.

A metal, preferably stainless steel, ring 8 is attached to one end of the lubricous elastic membrane using a suitable attach method such as compression attach between a stainless steel washer and the ring by use of screws and the ring 8, is slidably deployed in the space between the inner catheter 6 and outer catheter 4. The ring 8 is further connected to stainless steel pull wires 5. Typically, the attachment of the stainless steel ring 8 to the stainless steel pull wires is by welding of the wires to the appropriate locations on the ring; however, it will be appreciated that other techniques may be used to attach the steel ring with the pull wires. Although two pull wires are shown in FIG. 2, it will be appreciated that one pull wire or more than two pull wires may be used. Additional pull wires can be used to increase the uniformity of the force applied to the ring 8 during the pullback motion.

During the insertion phase of the stent deployment device, the guide wire 7 is initially inserted into the lumen through an appropriate entry location on the body and guided to the location where the stent deployment is needed. The rest of the deployment device is guided to the deployment location over the guide wire 7, as shown in FIG. 1. The guide wire 7 is advanced to the correct location and once in place is used to guide the catheter assembly with the crimped stent to the treatment location.

Figure 3:
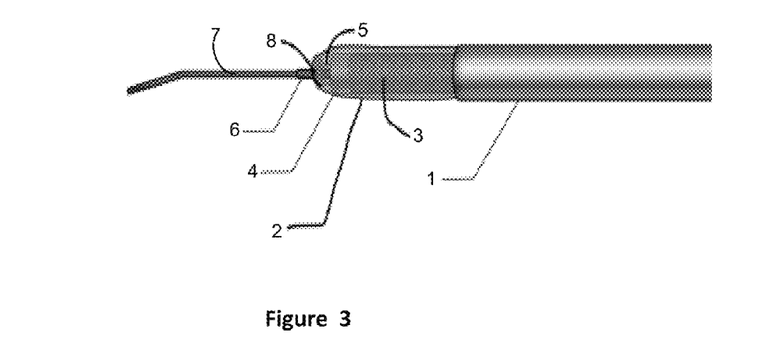
FIG. 3 is a side view of a partially extended outer catheter of the stent deployment device according to one embodiment of the invention.
Figure 8:
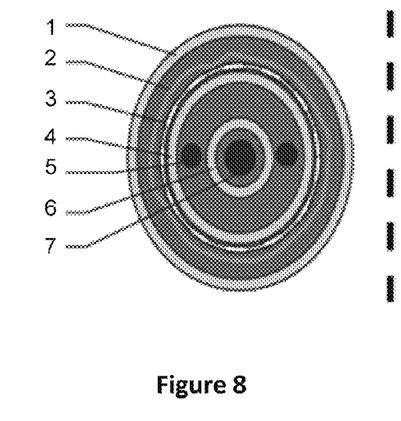
FIG. 8 is a cross-sectional view of the deployment device before the deployment of the stent according to one embodiment of the invention.

Once at the treatment location, the outer catheter 4 is extended from the sheath catheter 1 to expose the crimped stent 3, covered by the lubricous elastic membrane 2, as shown in FIG. 3 (diagrammatic view 300). As shown in FIG. 3, the end of the lubricous elastic membrane 2 is attached to the ring 8, slidably deployed between the inner catheter 6 and outer catheter 4. FIG. 8 shows a cross sectional view 800 of the device 300 prior to deployment of the stent 3. As shown in FIG. 8, the stent 3 is held in place over the outer catheter 4 by the presence of the lubricous elastic membrane 2.

Figure 4:
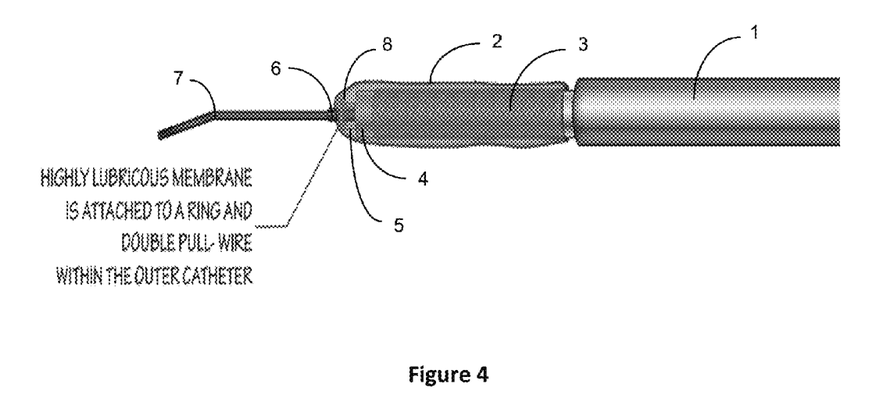
FIG. 4 is a side view of a fully extended outer catheter of the stent deployment device according to one embodiment of the invention.

FIG. 4 is a diagrammatic view 400, showing the outer catheter 4 fully extended from the sheath catheter 1, with the stent 3 exposed end to end but covered by the lubricous elastic membrane 2, holding the stent 3 in the crimped state. The proximal edge of the stent is now adjusted to align to the correct location in the lumen.

Figure 5:
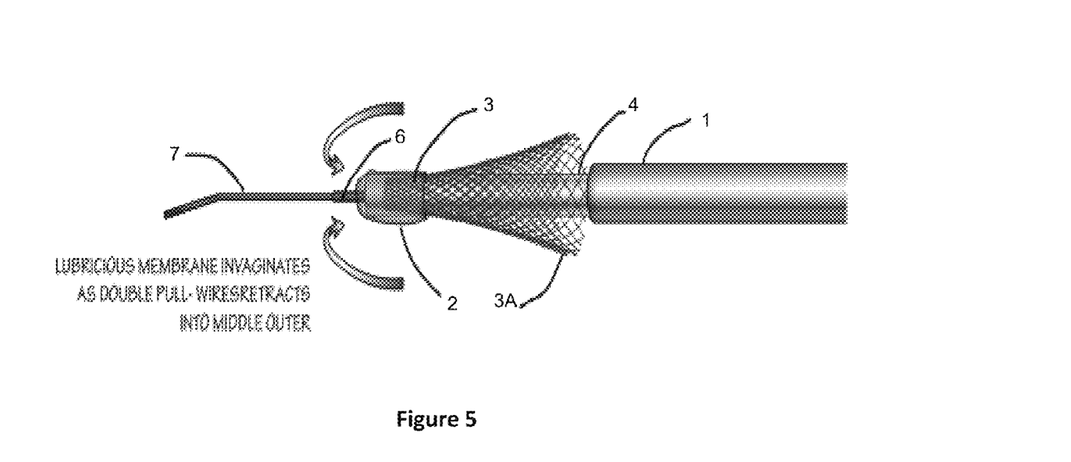
FIG. 5 is a side view of a partially proximal-to distal deployment of the stent according to one embodiment of the invention.

FIG. 5 is a diagrammatic view 500, showing the pullback pressure application to the pull wires 5. The pullback pressure is applied using a pull mechanism at the proximal edge of the sheath catheter 1. The pull wires 5 pullback the ring 8 into the space between the inner catheter 6 and outer catheter 4. The ring 8 pulls the lubricous elastic membrane 2 connected it behind it, allowing the lubricous elastic membrane 2 to invaginate into the space between the inner catheter 2 and the outer catheter 4. The lubricous elastic membrane 2 is pulled back from over the crimped stent 3, from the proximal edge to the distal edge, allowing the stent 3 to expand from the proximal edge and fixing the proximal edge accurately in place within the lumen.

Figure 6:
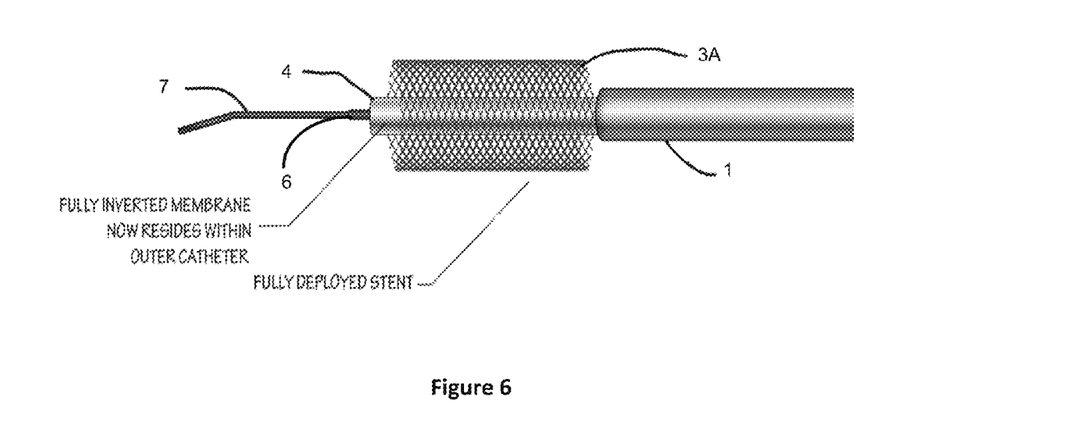
FIG. 6 is a side view of a fully expanded stent, expanded in a proximal to distal fashion in the location, according to one embodiment of the invention.

FIG. 6 is a diagrammatic view 600, showing the fully expanded stent 3 in place in the lumen. In FIG. 6, the lubricous elastic membrane (not shown) is pulled back into the space between the inner catheter 2 and outer catheter 4. The removal of the lubricous elastic membrane 2 from over the stent 3 releases both the proximal and distal end of the stent 3, in that order. The release allows the stent 3 to expand from its crimped state to its expanded state 3A in a proximal-to-distal fashion.

Figure 9:
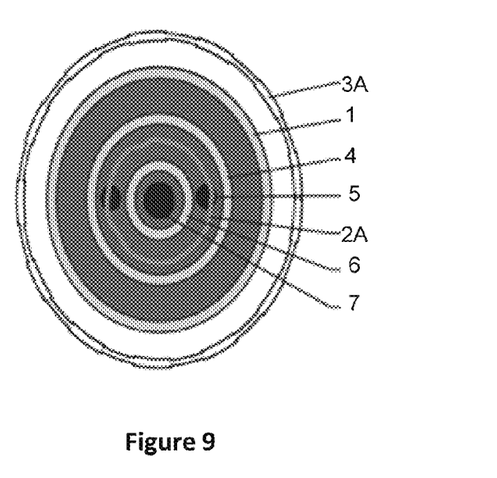
FIG. 9 is a cross sectional view of the deployment device during deployment according to one embodiment of the invention.

FIG. 9 is a cross-sectional view 900 of the stent deployment device after the stent 3 has been deployed in a proximal-to-distal fashion. The stent is shown in a fully expanded state 3A after deployment, and the inverted and invaginated lubricous elastic membrane 2A is shown in the inter space between the inner catheter 6 and the outer catheter 4.

Figure 7:
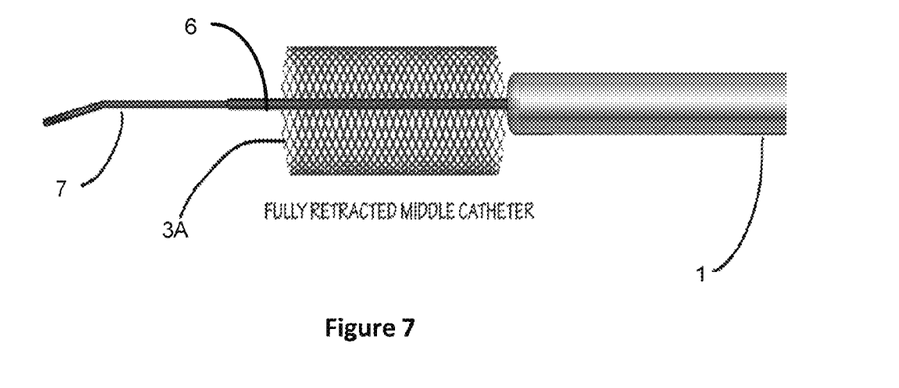
FIG. 7 is a side view of a fully deployed stent according to one embodiment of the invention.

FIG. 7 is a diagrammatic view of the released and deployed stent 3 A with the outer catheter 4 withdrawn into the sheath catheter as a first step in full deployment of the stent in the lumen and removal of the deployment device.

Figure 10:
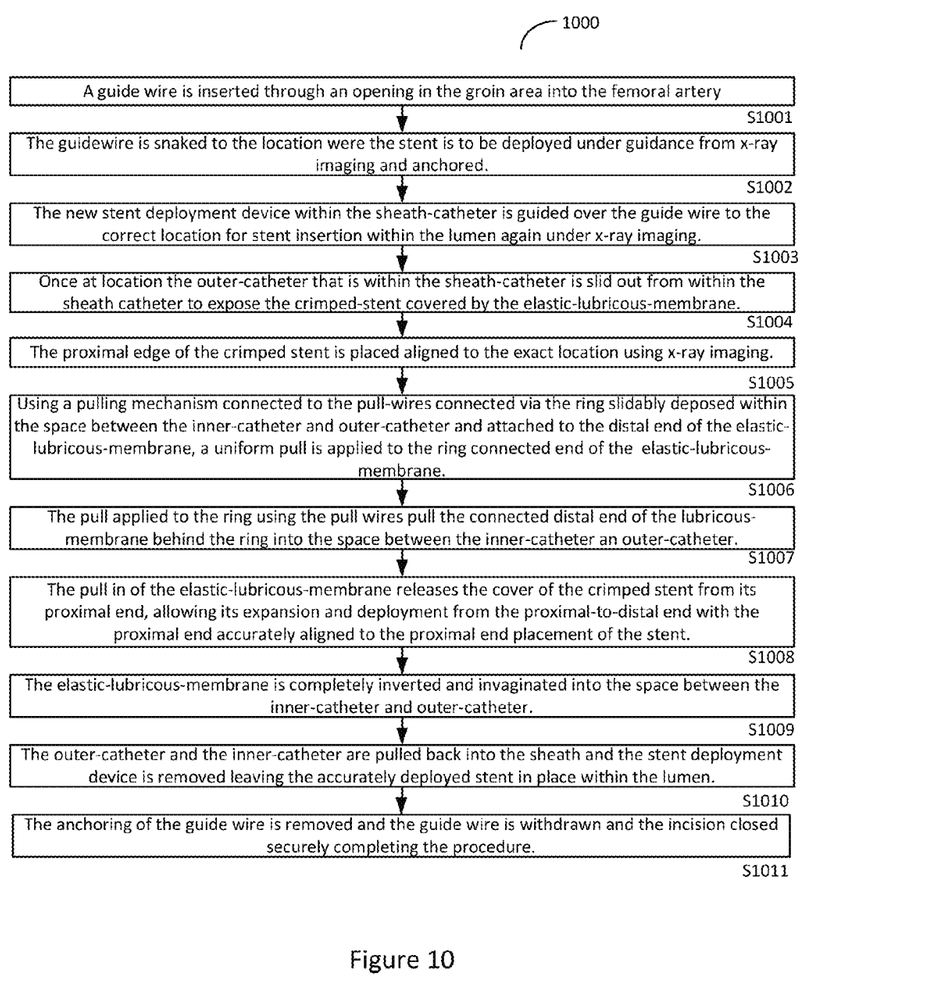
FIG. 10 is a flow chart of method for placement of a stent in a proximal-to-distal fashion according to one embodiment of the invention.

An exemplary method 1000 for deploying a stent in a proximal-to-distal manner according to an embodiment of the invention is shown in FIG. 10. It will be appreciated that the method 1000 may include additional or fewer steps than that shown in FIG. 10.

In one embodiment, a small opening or slit is made in the groin region of the patient to gain access to the femoral artery then a guide wire is inserted into the femoral femoral artery (block S1001).

The tip of the guide wire is advanced to the location where the stent is to be deployed and the guide wire is anchored in place (block S1002). The guide wire may have a region which is visible in an X-ray scanner, such that the guide wire is delivered to the location under guidance from X-ray imaging, as known to those of skill in the art.

The stent deployment device is guided over the guide wire to the correct location for stent insertion within the body lumen (block S1003). The stent deployment device may also be delivered to the location under X-Ray imaging guidance.

Once at the location, the outer catheter is slid out from within the sheath catheter to expose the crimped stent covered by the elastic-lubricous-membrane (block S1004). It will be appreciated that the outer sheath catheter itself is not a requirement for the stent deployment but is used typically to provide protection to the elastic-lubricous-membrane covering the stent in the new deployment device. In an embodiment that does not include a sheath catheter, this step may be skipped.

The method 1000 continues by aligning the proximal edge of the crimped stent to the exact location (block S1005). It will be appreciated that alignment may performed using x-ray imaging or other known stent delivery visualization techniques.

The method 1000 continues by applying a uniform pull to the ring on the elastic lubricous membrane using a pull mechanism (S1006). The pulling mechanism is connected to the pull wires at the proximal end of the sheath catheter and is connected to the ring, which is in turn attached to the distal end of the elastic lubricous membrane.

The pull applied to the ring using the pull wires pulls the ring and the elastic lubricous membrane into the space between the inner catheter and the outer catheter (block S1007).

The pull applied to the elastic lubricous membrane releases the cover of the crimped stent from its proximal end, allowing its expansion and deployment from the proximal-to-distal end with the proximal end accurately aligned to the proximal end placement location of the stent within the body lumen (block S1008).

The elastic lubricous membrane is completely inverted and invaginated into the space between the inner catheter and outer catheter behind the connected ring (block S1009).

The outer catheter and the inner catheter are pulled back into the sheath catheter and the stent deployment device is removed, leaving the stent accurately deployed in place within the body lumen (block S1010).

The anchoring of the guide wire is removed and the guide wire is withdrawn and the incision closed securely completing the procedure (block S1001). The stent is left accurately deployed in the body lumen, thereby completing the procedure.

While the invention has been described in terms of several embodiments, those of ordinary skill in the art will recognize that the invention is not limited to the embodiments described, but can be practiced with modification and alteration within the spirit and scope of the appended claims. The description is thus to be regarded as illustrative instead of limiting. There are numerous other variations to different aspects of the invention described above, which in the interest of conciseness have not been provided in detail. Accordingly, other embodiments are within the scope of the claims.

The invention has been described in relation to particular examples, which are intended in all respects to be illustrative rather than restrictive. Those skilled in the art will appreciate that many different combinations will be suitable for practicing the present invention. Other implementations of the invention will be apparent to those skilled in the art from consideration of the specification and practice of the invention disclosed herein. Various aspects and/or components of the described embodiments may be used singly or in any combination. It is intended that the specification and examples be considered as exemplary only, with a true scope and spirit of the invention being indicated by the following claims.

What is claimed is:

1. A stent deployment system comprising:
    an inner catheter slideably movable over a guide wire;
    an outer catheter slideably moveable over the inner catheter such that an interspace is formed between the inner catheter and the outer catheter;
    an expandable stent crimped on the outer catheter;
    a lubricous elastic membrane removably covering the stent, the lubricous elastic membrane having a proximal end and a distal end;
    a ring slidably deployed over the inner catheter and retractable into the interspace, the ring attached to the distal end of the lubricous elastic membrane;
    a plurality of pull wires connected to the ring, for retracting the ring and elastic membrane into the interspace.

2. The system of claim 1, further comprising a sheath catheter, the outer catheter slideably movable within the sheath catheter.

3. The system of claim 1, further comprising the guide wire.

4. The system of claim 1, wherein the plurality of pull wires comprises two pull wires.

5. The system of claim 1, further comprising a pull mechanism connected to the proximal end of the pull wires and for applying a pullback force for retracting the ring and elastic membrane into the interspace.

6. The system of claim 1, wherein the membrane is invertible.

7. A method of using the deployment device of claim 1 to deploy a stent in a proximal-to-distal fashion.

8. A method comprising:
    delivering a stent deployment device to a treatment location, the stent deployment device comprising an inner catheter, an outer catheter, a stent attached to the outer catheter, a membrane covering the stent, a ring attached to a distal end of the membrane, and a plurality of wires attached to the ring and extending through a space between the inner catheter and the outer catheter;
    aligning a proximal edge of the stent to the treatment location; and
    retracting the ring and the membrane into the space between the inner catheter and the outer catheter using the plurality of wires to expand the stent from its proximal end to its distal end.

9. The method of claim 8, wherein the membrane covers and retains the stent in a crimped state over the outer catheter prior to retraction.

10. The method of claim 8, wherein the ring and plurality of wires pull the membrane to retract the membrane from over the stent in a proximal to distal fashion.

11. The method of claim 8, wherein retraction of the ring inverts and invaginates the membrane.

12. The method of claim 8, further comprising:
    sliding the outer catheter out from within a sheath catheter to expose the stent.

13. The method of claim 8, further comprising:
    forming a small opening in the groin region of the patient to gain access to the femoral artery; and
    inserting a guide wire into the femoral artery.

14. The method of claim 8, further comprising:
    advancing a tip of a guide wire to the treatment location; and
    anchoring the guide wire at the treatment location.

15. The method of claim 14, wherein the guide wire is advanced under guidance from X-ray imaging.

16. The method of claim 14, wherein the stent deployment device is delivered to the treatment location over the guide wire.

17. The method of claim 8, wherein the proximal edge of the stent is aligned to the treatment location using X-ray imaging.

18. The method of claim 8, wherein a pull mechanism is used to apply a pull force to the plurality of wires to retract the ring and membrane.

19. The method of claim 18, wherein the pull force applied to the ring is uniform.

20. The method of claim 8, further comprising:
    removing the stent deployment device, leaving the stent accurately deployed in place within the body lumen.

* * * * *